United States Patent [19]

Baldauf et al.

[11] 4,069,701

[45] Jan. 24, 1978

[54] PORTABLE AGENT GENERATOR

[75] Inventors: Frederick C. Baldauf, Bel Air; Kwok Y. Ong, Aberdeen, both of Md.

[73] Assignee: The United States of America as represented by the Secretary of the Army, Washington, D.C.

[21] Appl. No.: 720,543

[22] Filed: Sept. 7, 1976

[51] Int. Cl.² .......................................... G01N 31/00
[52] U.S. Cl. ................................. 73/1 G; 261/121 R
[58] Field of Search ............. 73/1 G; 261/121 R, 153

[56] References Cited

U.S. PATENT DOCUMENTS

| | | | |
|---|---|---|---|
| 2,853,873 | 9/1958 | Hallobaugh et al. | 73/1 G |
| 2,981,526 | 4/1961 | Grumbach | 261/121 R |
| 3,611,790 | 10/1971 | Brouwer et al. | 73/1 G |
| 3,614,855 | 10/1971 | Van Luik, Jr. | 73/1 G |
| 3,665,748 | 5/1972 | Mator | 73/1 G |
| 3,674,435 | 7/1972 | Van Luik, Jr. et al. | 73/1 G |

Primary Examiner—Daniel M. Yasich
Attorney, Agent, or Firm—Nathan Edelberg; Kenneth P. Van Wyck

[57] ABSTRACT

A test agent generation system capable of producing a low constant vapor of test agent for use in a method of calibrating and checking the GB agent sensitivity of a point-source alarm system.

11 Claims, 1 Drawing Figure

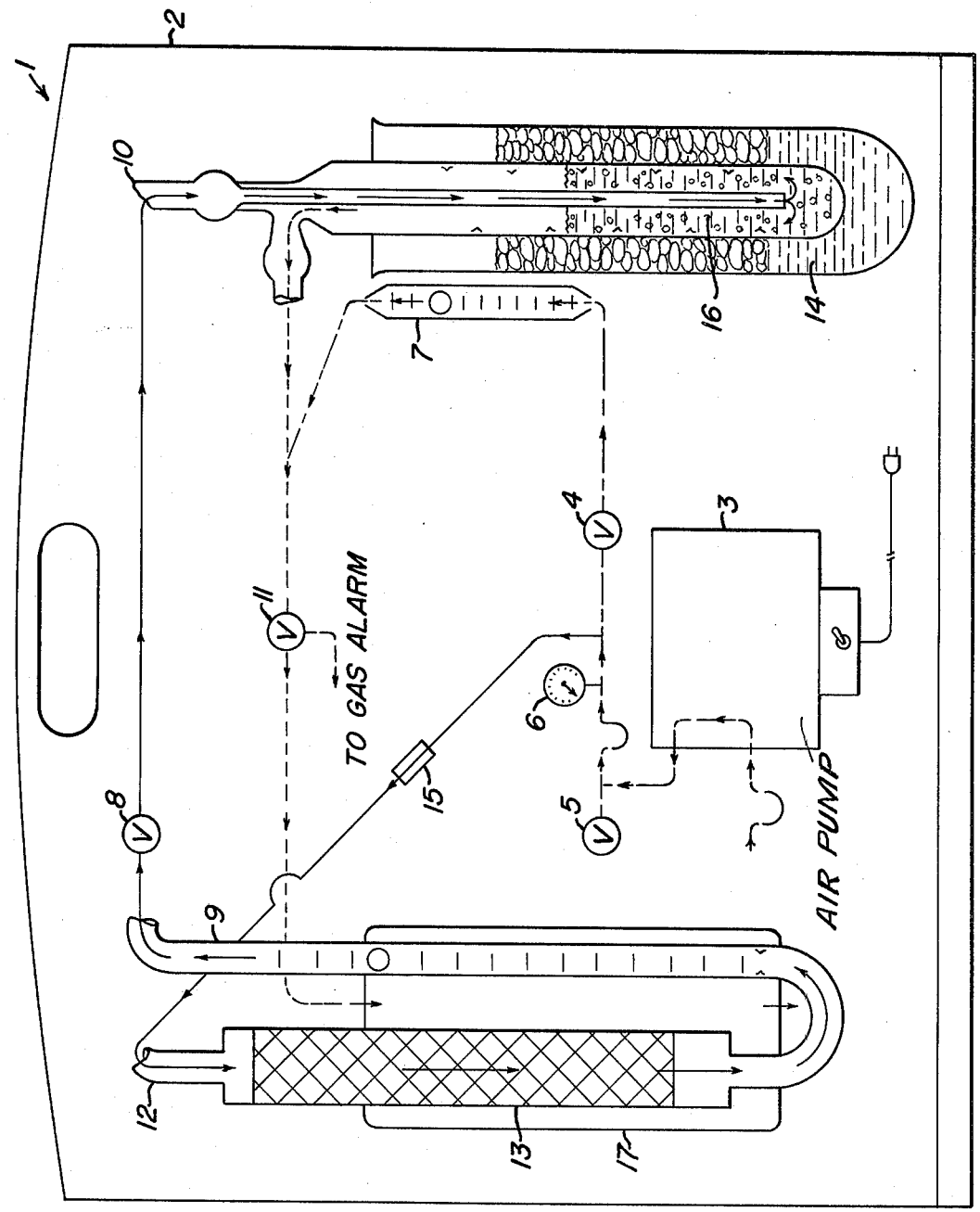

PORTABLE AGENT GENERATOR

DEDICATORY CLAUSE

The invention described herein may be manufactured, used, and licensed by or for the Government for governmental purposes without the payment to us of any royalty thereon.

DESCRIPTION OF THE INVENTION

Our invention relates to a test agent generation system for producing a low constant vapor of test agent for use in calibrating and checking the GB sensitivity of point-source alarm systems.

Our invention further relates to a portable gas dilution apparatus for rapidly generating a low, stable, constant flow of test agent vapor.

The problem of reliably determining minimum GB toxic agent detection capability of point-source alarm systems on-site has always existed in the field and at demilitarization installations where the alarms are being used to give warnings during work operations.

Several prior art methods have been used for determining the GB toxic agent detection capability of an alarm in the field. Quinine sulfate solutions have been used to check point-source agent alarms by directly introducing the solution, which is capable of producing fluorescence, into the cell. The quinine sulfate solutions are only useful in checking the optical and electrical systems of the alarm. The quinine sulfate solutions do not check the alarm systems capability to take a sample from the atmosphere, extract a suspected GB agent from the air, and chemically reacting the GB agent with the alarm system.

Various devices containing GB agent under static conditions, either in solution or in an adsorbent material, have been used to provide a test vapor, but have been proven not to be reliable for producing the low, constant vapor of GB agent required for use in determining the minimum detectable concentration of the alarm in the field. The vapor output from these devices is changeable to a degree from changes in air temperature. In addition, the generator vapor, when not in use, is contained under static conditions and consequently, the vapor eluted under the sample flow rate conditions could not be at equilibrium.

On a laboratory scale, the standard method of generating low, constant, and reliable concentrations of GB is with a vapor dilution apparatus which is constructed almost entirely of glass and contains the agent in a pure form. This laboratory apparatus is fragile, not readily transportable and requires a 24 hour period to stabilize after initial servicing with agent. Additionally, lengthy equilibration times are required for each adjustment to change vapor concentrations.

The present invention was conceived and reduced to practice to solve the aforementioned problems and to satisfy the long felt need for a readily transportable agent generation system that can produce a low, constant vapor of test agent at a fast equilibration time and a concentration directly related to the air flow rate used.

The principal object of our invention is to provide an agent generation system and method for calibrating and testing the GB agent sensitivity of a point-source agent alarm system.

Another object of our invention is to provide an agent generation system which is readily transportable, easy to operate and capable of producing a low constant flow of agent at a desired concentration within a relatively fast equilibration time.

A further object of our invention is to provide a portable gas dilution apparatus that can produce a constant flow of gas at any desired concentration by regulating the air flow rate.

A still further object of our invention is to provide a portable agent generation system which can be used in the field to produce controlled concentrations of pollutants for testing and calibrating environmental monitoring equipment.

Other objects and advantages of our invention will become apparent from the following detailed description of the invention.

The drawing is a schematic view of our portable agent generation apparatus.

The generator of our invention, as shown in the drawing, is a portable gas dilution apparatus which will be described in detail as follows.

The complete generator apparatus 1 of our invention is mounted on a vertical frame 2 with handle cut out and consists of an air pump 3 which supplies a regulated, pressurized air flow to agent bubbler 10 through pressure valve 5 and air dilution control valve 4, which are monitored by gage 6, to in-line orifice 15 which is used to limit flow through the charcoal filter 13 in drierite column 12 to the agent bubbler (reservoir) 10 through flowmeter 9 and needle valve 8. The air flows through the dilute liquid agent solution 16 in the agent bubbler, which is maintained in an ice bath within dewar 14, and is diluted with air from air pump 3 through air dilution control valve 4 and air flowmeter 7. The air diluted agent vapor thus produced by the instant generator is extracted from the system at stopcock sample port 11 to be used in the point-source gas alarm, not shown, and any excess agent vapor is filtered through charcoal cannister 17 before being released to the atmosphere.

The portable agent generator operates, as shown in the drawing, from regulated, pressurized air supplied by the small air pump 3, e.g., 100v.ac. Following start-up of the pump, the air dilution control valve 4 is open until flowmeter 7 indicates approximate desired air dilution. Adjustments are then made by alternating between valves 4 and 5 until a pressure of 2-3 p.s.i.g. is obtained on gage 6 and air flowmeter 7 indicates the desired air dilution. The needle valve 8 is then opened until flowmeter 9 indicates the desired air flow to the agent bubbler (reservoir) 10 and the system is then allowed to equilibrate for 5-15 minutes before use. Upon equilibration, the generator is calibrated by collecting agent from the stopcock sample port and performing conventional analysis to determine precise concentration of the agent.

In the preferred method of operation, the air flowed to the agent bubbler is limited, as a safety factor, to 300 ml./min. by the in line orifice 15. The air flow is monotored through flowmeter 9 and is bubbled through 10 ml. of GB (Isopropyl methyl phosphonofluoridate) solution 16 (normally 2% GB in hexylene glycol) in the agent bubbler 10. The temperature of the GB agent solution is maintained constant by an ice bath contained in Dewar 14. The agent vapor eluted from the bubbler is diluted with large amounts of metered air to produce a resulting diluted vapor mixture of approximately 1.0 mg./liter.

The operation of the portable gas dilution apparatus can be adjusted to increase the agent vapor concentration, by performing one or more of the following steps: increasing the air flow to the agent bubbler by means of needle valve 8; decreasing the air dilution by regulating air dilution control valve 4 and pressure valve 5; increasing the liquid agent concentration in the agent bubbler 10; or increasing the bath temperature within dewar 14 in the agent bubbler system.

The complete portable gas dilution apparatus of this invention, mounted on a vertical frame, typically measures approximately 8 inches × 18 inches × 17 inches high, i.e., 20.3 cm × 45.7 cm × 43.2 cm and weighs approximately 23 lbs (10.4 kg.). The air pump, metering valves, air flowmeters, agent bubbler (reservoir), drierite column and charcoal type filter of our invention are conventional. The air supply source can include a compressed air tank or house-air line.

The portable generator of our invention has utility as a field apparatus in producing controlled concentrations of pollutants for checking or calibrating environmental monitoring equipment on-site.

The essential features of our portable agent generator are the formation of a low, stable concentration of agent vapor within a rapid equilibration time and the ease of adjustment of the vapor concentration utilizing direct flowmeter readings.

The particular details of the method of construction of the generator, and size and shape of the unit, do not form a critical feature of this invention and can be varied within the scope of the invention. Similarly, the pressure valves, flowmeters, air pumps and the like are conventional units which are commercially available and can be varied within the skill of one in the related art.

It is obvious that other modifications can be made of our invention, and we desire to be limited only by the scope of the appended claims.

We claim:

1. A self-contained system for generating a dilute agent vapor of desired concentration for use in calibrating and testing the sensitivity of an agent point-source alarm by the agent vapor consisting essentially of an air supply source for providing an air flow to the system; valves for regulating said air flow; a drierite column and charcoal filtering means for purifying said air flow; a flowmeter to regulate the flow of said purified air to a bubbler means, the bubbler means containing a dilute liquid agent solution through which said air flow is bubbled to produce an agent vapor; cooling means attached to said bubbler for maintaining the liquid agent solution within the bubbler at a constant temperature; a interconnected means for adding a regulated flow of air to said agent vapor to produce a dilute agent vapor of desired concentration and a means for flowing said dilute agent vapor from the system to a point-source agent alarm.

2. The system of claim 1 further including an in-line orifice for limiting the air flow from the air supply source to the drierite column and charcoal filtering means.

3. The system of claim 1 wherein the cooling means is an ice-bath container in which the bubbler is disposed.

4. The system of claim 1 wherein the air supply source is an air pump.

5. The system of claim 1 wherein the air supply source is a compressed air tank.

6. A method for generating a low, stable concentration of agent vapor within a fast equilibration time for use in calibrating and testing the sensitivity of a agent alarm system comprising the steps of providing a source of air to a system for generating a dilute agent vapor, the system including the steps of regulating the flow of said air to a bubbler by means of valves and an air flowmeter; flowing the air through a charcoal filter and a drierite column to filter said air; flowing the filtered air through the flowmeter to provide a constant flow of air to the bubbler; bubbling the air through a dilute agent solution within the bubbler to produce an agent vapor; diluting the agent vapor eluted from the bubbler by adding a regulated flow of air to said agent vapor to produce a dilute agent vapor of desired concentration and subsequently introducing said dilute agent vapor into the agent alarm.

7. The method of claim 6 wherein the steps of providing air to the bubbler and the step of diluting the agent vapor by adding a regulated flow of air utilizes air provided by a single air supply source.

8. The method of claim 7 wherein the air supply source is selected from the group consisting of a air pump means, a compressed air tank and a house-air line.

9. The method of claim 8 wherein the air supply source is an air pump.

10. The method of claim 6 wherein the solution within the agent bubbler is a dilute isopropyl methyl phosphonofluoridate (GB) solution in hexylene glycol.

11. The method of claim 10 wherein the agent is present in a 2% solution and the flow of air is regulated to give a dilute agent vapor concentration of approximately 1 mg/liter.

* * * * *